United States Patent [19]

Dror et al.

[11] Patent Number: 5,755,939
[45] Date of Patent: May 26, 1998

[54] POLYION SENSOR WITH MOLECULAR WEIGHT DIFFERENTIATION

[75] Inventors: Michael Dror; Robert F. Baugh, both of Parker, Colo.

[73] Assignee: Medtronic, Inc., Minneapolis, Minn.

[21] Appl. No.: 640,273

[22] Filed: Apr. 30, 1996

[51] Int. Cl.⁶ ........................................ G01N 27/26
[52] U.S. Cl. ............................ 204/418; 422/82.03
[58] Field of Search ..................... 204/418; 422/82.03

[56] References Cited

U.S. PATENT DOCUMENTS 5,236,570  8/1993  Ma et al. ............................ 204/418
5,453,171  9/1995  Ma et al. ............................ 204/418
5,531,870  7/1996  Cha .................................... 204/418

*Primary Examiner*—Bruce F. Bell

[57] ABSTRACT

An ion selective electrode membrane is selective to polyions in a limited molecular weight range. The membrane is formed by a heparin polyion selective polymeric layer and an outer filter layer permeable to polyions of limited molecular weight range. The outer filter may be cellulose acetate while the polyion selective membrane is a polyvinyl chloride containing plasticizer and a quaternary ammonium salt.

20 Claims, 1 Drawing Sheet

POLYION SENSOR WITH MOLECULAR WEIGHT DIFFERENTIATION

BACKGROUND OF THE INVENTION

1. Field of the Invention

The present invention relates to organic membrane type polyion selective electrodes. More specifically the present invention relates to polymer membrane type polyion selective electrodes suitable for monitoring polymeric macromolecules such as the polysaccharide heparin.

2. Brief Description of the Prior Art

Anion exchange selective polymeric membranes which are specific for ionic macromolecules, specifically heparin, are disclosed in U.S. Pat. No. 5,236,570, issued Aug. 17, 1993, and U.S. Pat. No. 5,453,171, issued Sep. 26, 1995. Both of these patents disclose heparin selective membranes formed of a polymeric material, a plasticizer and a quaternary ammonium chloride such as tridodecyl methyl ammonium chloride. A membrane is formed and mounted on the end of an electrode tube inserted in a sample solution such as blood containing unknown amounts of heparin. The potentiometric response between the membrane electrode and a reference electrode is a function of the concentration of heparin ions in the sample solution. The concentration is determined by reference to a standard curve established by measuring the EMF of solutions of known heparin concentrations.

OBJECTS OF THE INVENTION

It is the principal object of the present invention to detect and quantitatively measure concentrations of low molecular weight heparin in blood samples.

Another object of the present invention is to provide a sensor capable of sensing only a fraction of polyion molecules, specifically those having molecular weights below a predetermined molecular weight, in a solution.

SUMMARY OF THE INVENTION

In accordance with the foregoing objects, a polyion selective electrode, such as an electrode sensitive to heparin, is formed by an electrode tube with a silver/silver chloride (Ag/AgCl) electrode inserted into said tube from one end thereof. A polyion selective membrane sensitive to heparin closes the other end of the tube, and the electrode is contained in a saline solution in the tube. The polyion selective membrane has a predetermined molecular weight filter coating thereon so that the polyion selective membrane senses only polyions of a given molecular weight range. To this end, the membrane includes a cellulose acetate layer having a predetermined porosity capable of selectively determining the molecular weight cutoff of polyions to be subjected to the polyion sensitive membrane. Such a molecular weight filter layer is preferably formed by a porous polymer film having a porosity designed to pass low molecular weight heparin and bar high molecular weight heparin. Preferably, the filter layer is a commercially available filter having a predetermined molecular weight cutoff.

The membrane is formed by casting a film of a desired plasticized polyvinyl chloride on an acetate membrane of the desired thickness and porosity. A polyvinyl chloride membrane of the following composition is applied: 65% polyvinyl chloride, 33.5% of the plasticizer dioctyl sebacate, and 1.5% of the quaternary ammonium chloride, tridodecyl methyl ammonium chloride. The polyvinyl chloride is applied as a solution that is cast onto the cellulose acetate to form a film of a desired thickness. From the combination cellulose acetate/polyvinyl chloride film a disk is cut and applied to the open end of a polyvinyl chloride (PVC) sensor tube, so that when the PVC surface is bonded to the tube the cellulose acetate surface is facing outside, thereby forming a membrane on the end of the tube as described in U.S. Pat. Nos. 5,236,570 and 5,453,171. The electrode is used as described in the patents to sense the heparin content of solutions such as blood, however, the membrane will limit the sensed heparin to heparin having a molecular weight of less than the molecular weight cutoff, e.g. 5,000.

By comparing the results obtained with the cellulose acetate layered sensor and the conventional sensor, a more complete analysis of the heparin solution can be obtained, specifically learning about the molecular weight distribution of the analyzed heparin.

By selecting a cellulose acetate polymer, various ranges of molecular weights can be selectively determined.

DESCRIPTION OF THE PREFERRED EMBODIMENT

Figure 1:
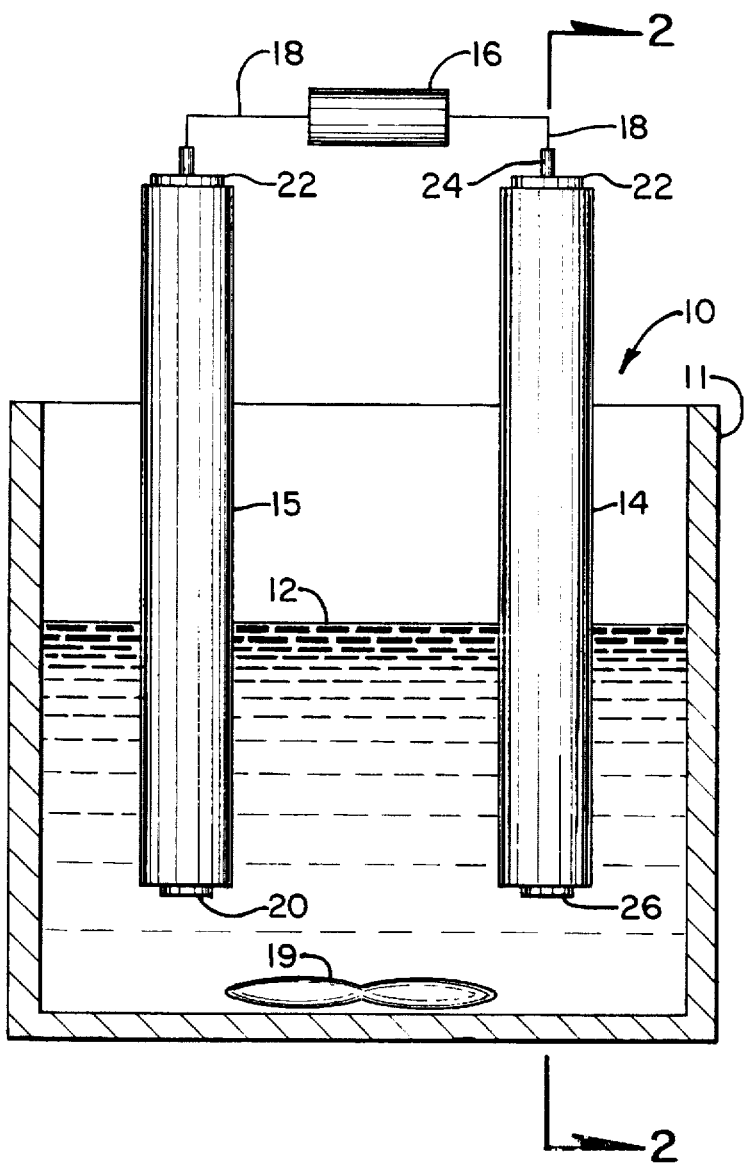
FIG. 1 is a schematic view of a heparin detection potentiometric circuit including a heparin detection electrode, a potentiometer and a reference electrode, the electrodes being inserted in a solution in a container.

In accordance with the foregoing objects, the present invention is embodied in a test cell 10 formed by a container 11 containing a heparin solution 12 to be tested. A heparin sensitive electrode 14 and a reference electrode 15 are inserted into the heparin solution bath. The electrodes are connected in series with a potentiometer 16, such as a pH meter, by appropriate wires or conductors 18. A magnetic stirrer 19 in the bottom of the container stirs and circulates the heparin solution. An alternative mode of testing involves immersing electrodes 14, 15 in a nonstirred solution. (See FIG. 1).

The reference electrode 15 may be of any appropriate construction such as a calomel or double junction silver/silver chloride (Ag/AgCl) reference electrode having a conductive plate 20 at the end thereof. The reference electrode is also inserted in the blood and heparin solution and connected to the potentiometer.

Figure 2:
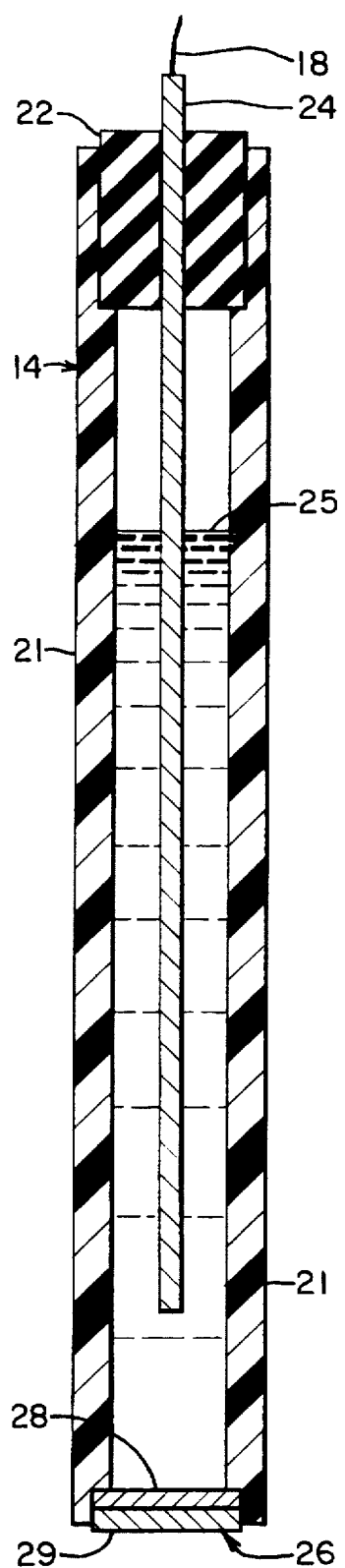
FIG. 2 is an enlarged section view taken substantially in the plane of line 2—2 on FIG. 1

The heparin sensor electrode 14, as shown in cross-section in FIG. 2, is formed by an elongated tubular housing 21 formed of polyvinyl chloride or like impervious material. At its upper end the tube 21 supports a cap 22 which in turn carries an elongated silver/silver chloride (Ag/AgCl) electrode 24 inserted into sodium chloride solution 25 contained within the tubular housing 21.

In accordance with the present invention, the lower end of the heparin sensor electrode tube 21 is closed by a heparin selective multilayer polymer membrane 26 having a polyanion selective layer 28 and a cellulose acetate molecular weight filter 29. The membrane is prepared by applying on top of a selected cellulose acetate film a heparin selective membrane prepared according to U.S. Pat. Nos. 5,236,570 and 5,453,171. A disk of the multilayer membrane is cut from the cast films and applied to the lower end of the tube 21 utilizing a tetrahydrofuran solvent to effect adhesion of the membrane to the tube.

The presence of heparin having a molecular weight below the selective molecular weight of the cellulose acetate filter 29 in the blood solution 12 creates an electromotive force (EMF) across the heparin selective membrane which EMF is measured and indicated by the potentiometer 16 in the electrical circuit formed by the heparin blood solution, electrodes 14, 15, connector 18 and potentiometer 16. The voltage potential or EMF indicated by the potentiometer 16 is a function of the concentration of heparin of a particular molecular weight range in the blood and heparin solution 12.

While a certain illustrative embodiment of the present invention has been described above, it should be understood that there is no intention to limit the invention to the specific forms disclosed. On the contrary, the intention is to cover all modifications, alternatives, equivalents and uses falling within the spirit and scope of the invention as expressed in the appended claims.

We claim:

1. An ion-selective electrode comprising an electrode membrane selective to polyionic macromolecules having a molecular weight of less than a set molecular weight, said membrane comprising a polyion-selective polymeric layer and an outer filter layer permeable to said polyionic macromolecules.

2. An electrode as defined in claim 1, wherein said outer filter layer is a commercial filter having a set molecular weight cutoff.

3. An electrode as defined in claim 1, wherein said outer filter layer is formed of cellulose acetate.

4. An ion-selective electrode of claim 1, wherein said polyionic macromolecule is heparin.

5. An ion-selective electrode of claim 1, wherein said polyion-selective polymeric layer is selective for heparin.

6. An ion-selective electrode of claim 5, wherein said polyion-selective polymeric layer comprises a quaternary ammonium chloride salt.

7. An ion-selective electrode of claim 6, wherein said quaternary ammonium chloride salt is tridodecyl methyl ammonium chloride.

8. An ion-selective electrode of claim 7, wherein said tridodecyl methyl ammonium chloride is present in a weight percent of 1.5 percent.

9. An ion-selective electrode of claim 6, wherein said polyion-selective polymeric layer further comprises polyvinyl chloride.

10. An ion-selective electrode of claim 9, wherein said polyvinyl chloride is present in a weight percent of 65 percent.

11. An ion-selective electrode of claim 6, wherein said polyion-selective polymeric layer further comprises a plasticizer.

12. An ion-selective electrode of claim 11, wherein said plasticizer is dioctyl sebacate.

13. An ion-selective electrode of claim 12, wherein said dioctyl sebacate is present in a weight percent of 33.5 percent.

14. An ion-selective electrode comprising an electrode membrane selective to polyionic macromolecules having a molecular weight of less than a set molecular weight, comprising a cellulose acetate filter layer and a polyanion-selective polymeric layer.

15. An ion-selective electrode of claim 14, wherein said polyionic macromolecule is heparin.

16. An ion-selective electrode of claim 14, wherein said polyanion-selective polymeric layer is selective for heparin.

17. An ion-selective electrode of claim 14, wherein said polyanion-selective polymeric layer comprises a quaternary ammonium chloride salt.

18. An ion-selective electrode of claim 17, wherein said quaternary ammonium chloride salt is tridodecyl methyl ammonium chloride.

19. An ion-selective electrode comprising an electrode membrane selective to heparin, wherein the heparin has a molecular weight of less than a set molecular weight said membrane comprising a cellulose acetate filter layer permeable to said heparin and a heparin-selective polymeric layer.

20. An ion-selective electrode of claim 19, wherein said heparin-selective polymeric layer comprises a quaternary ammonium chloride salt.

* * * * *